United States Patent
Kolata et al.

[11] Patent Number: 5,879,291
[45] Date of Patent: Mar. 9, 1999

[54] DEVICE USED WITH A SURGICAL RETRACTOR TO ELEVATE BODY PARTS

[75] Inventors: Ronald J. Kolata, Cincinnati; William D. Fox, New Richmond; Craig B. Berky, Milford; Gary W. Knight, West Chester; David L. Hamann, Cincinnati, all of Ohio

[73] Assignee: Ethicon Endo-Surgery, Inc., Cincinnati, Ohio

[21] Appl. No.: 946,767

[22] Filed: Oct. 8, 1997

[51] Int. Cl.⁶ ..................................................... A61B 17/00
[52] U.S. Cl. .......................... 600/227; 600/232; 600/201
[58] Field of Search ..................................... 600/201, 226, 600/227, 228, 231, 210, 232, 233, 234, 235

[56] References Cited

U.S. PATENT DOCUMENTS

| | | |
|---|---|---|
| Re. 34,150 | 12/1992 | Santilli et al. . |
| 439,028 | 10/1890 | Washington ............................ 600/227 |
| 1,030,530 | 6/1912 | Palmer ................................ 600/227 X |
| 4,622,955 | 11/1986 | Fakhrai ................................ 600/228 X |
| 4,865,019 | 9/1989 | Phillips .................................... 600/232 |
| 5,025,779 | 6/1991 | Bugge .................................. 600/232 X |
| 5,109,831 | 5/1992 | Forrest et al. . |
| 5,167,223 | 12/1992 | Koros et al. . |
| 5,503,617 | 4/1996 | Jako . |
| 5,520,610 | 5/1996 | Gigloi et al. . |

FOREIGN PATENT DOCUMENTS 70332  10/1915  Austria .................................. 600/228

Primary Examiner—Jeffrey A. Smith
Attorney, Agent, or Firm—Dean Garner

[57] ABSTRACT

In accordance with the present invention, there is provided a device for pivoting a surgical retractor with respect to a patient it is being used on. The device includes a bridge having distal and proximal ends wherein a distal coupling is attached to the distal end of the bridge and a proximal coupling is slidably attached to the bridge proximal to the distal coupling. The proximal and distal couplings include a means for releasably attaching itself to a surgical retractor. The device further includes a lifting assembly attached to the bridge proximal to the proximal coupling. The lifting assembly comprises a means for applying an upward force to the proximal coupling, whereby when the device is attached to a surgical retractor, the lifting assembly pivots the retractor upward about the distal coupling.

35 Claims, 9 Drawing Sheets

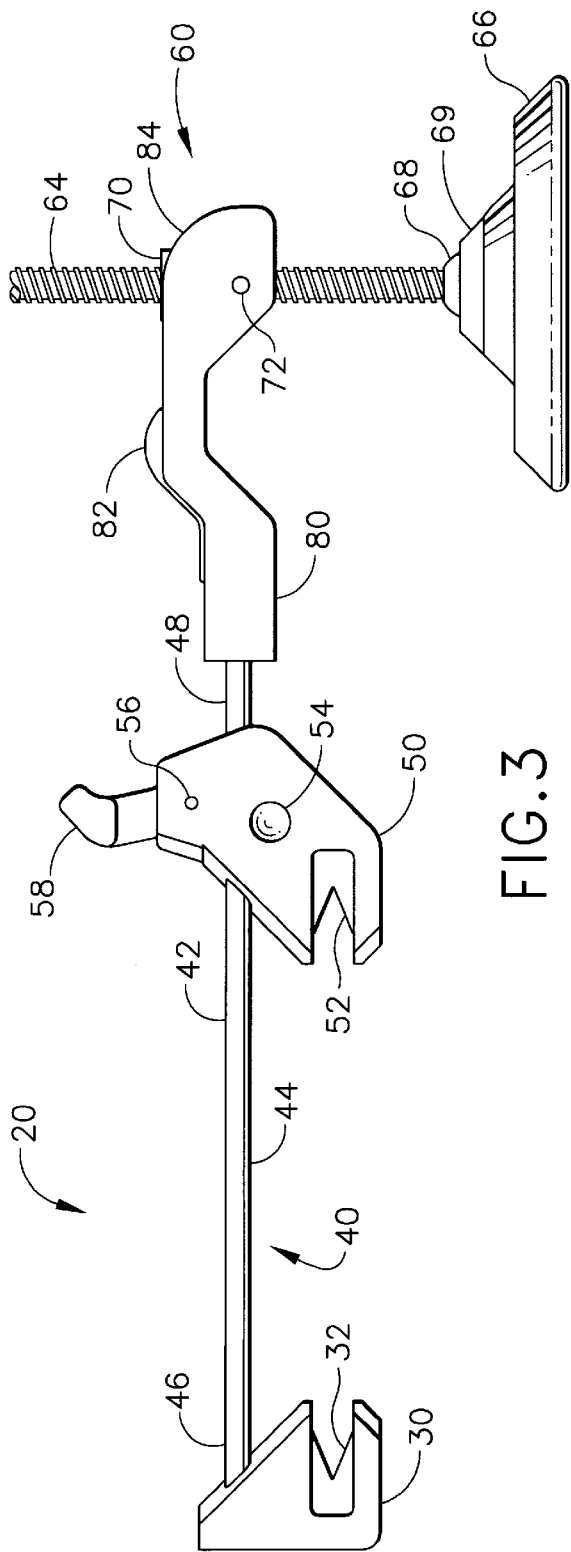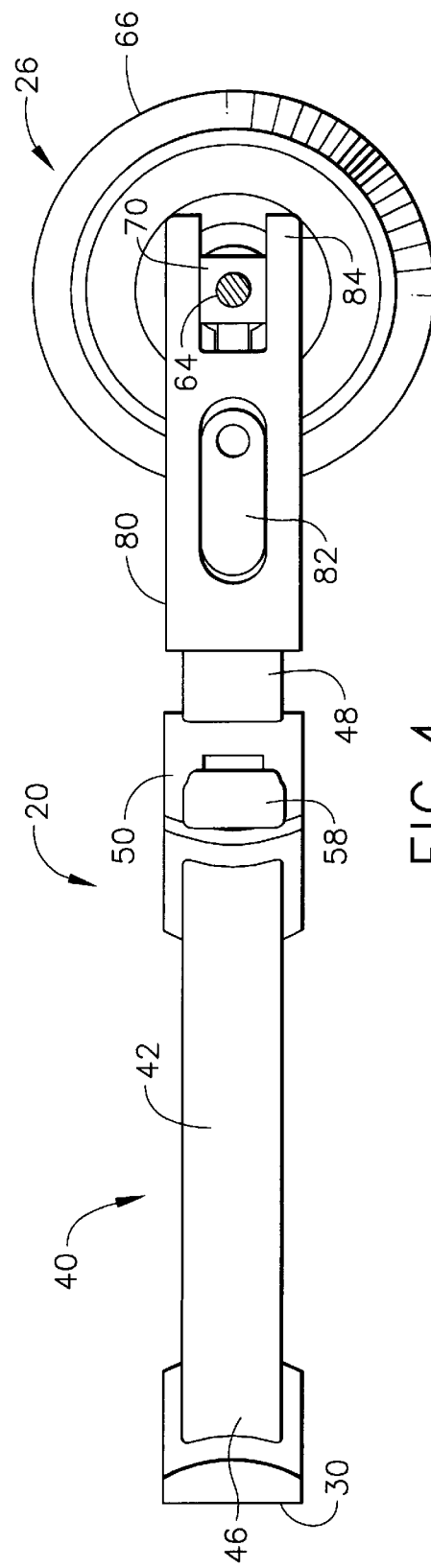

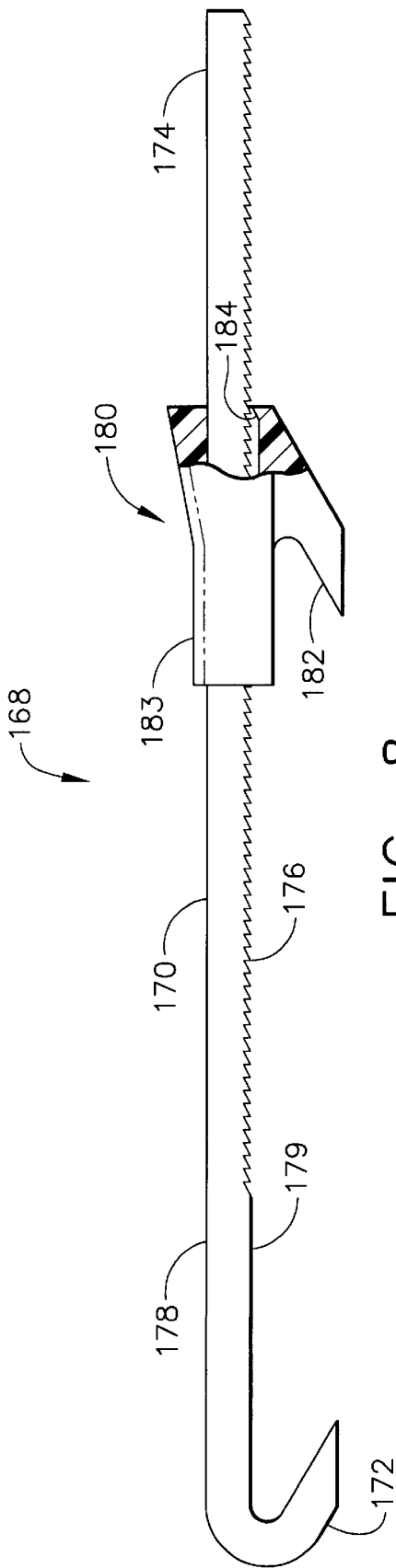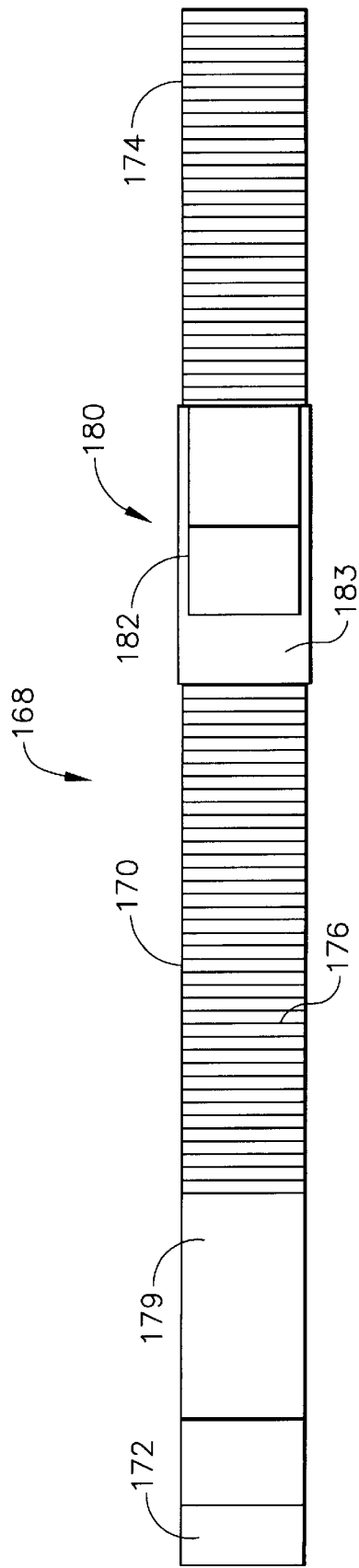

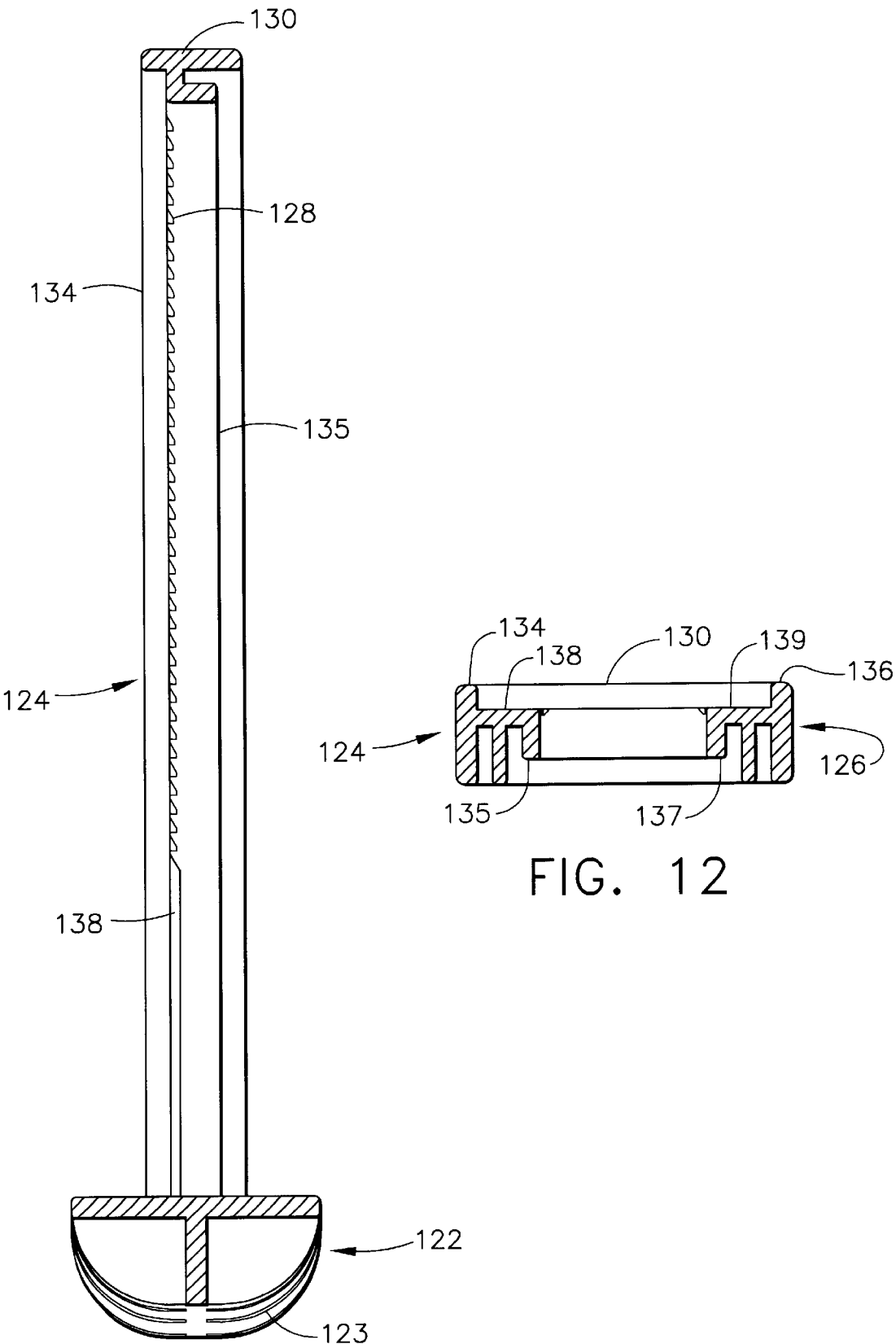

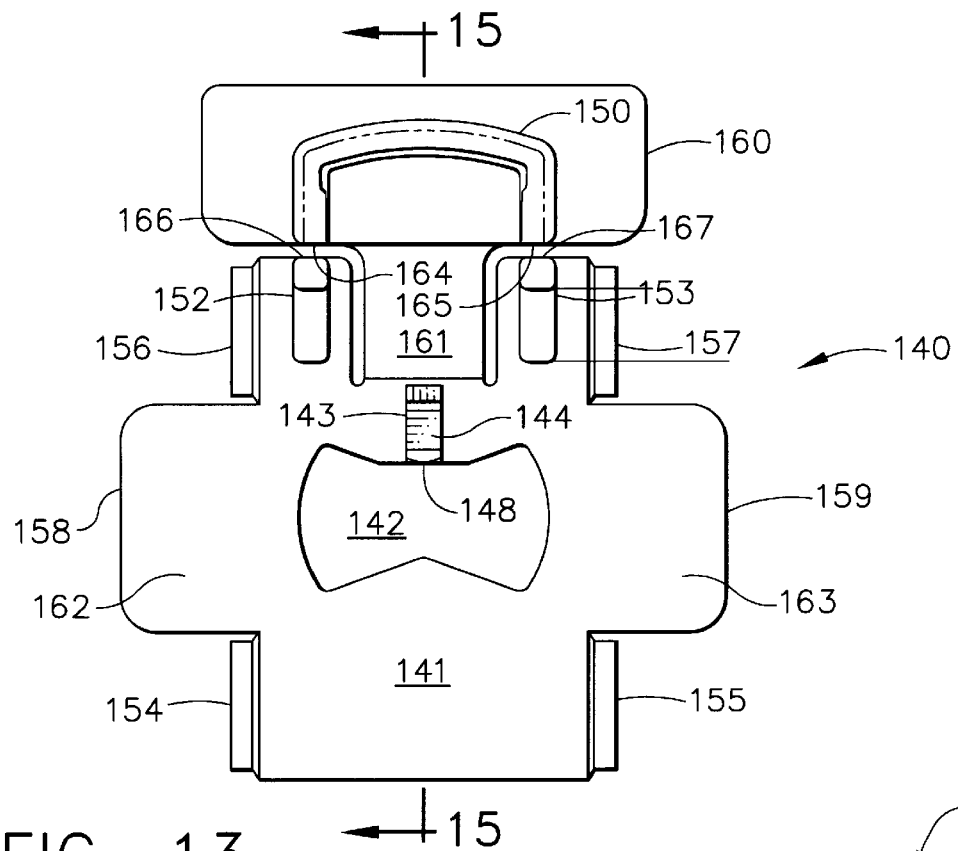
FIG. 13
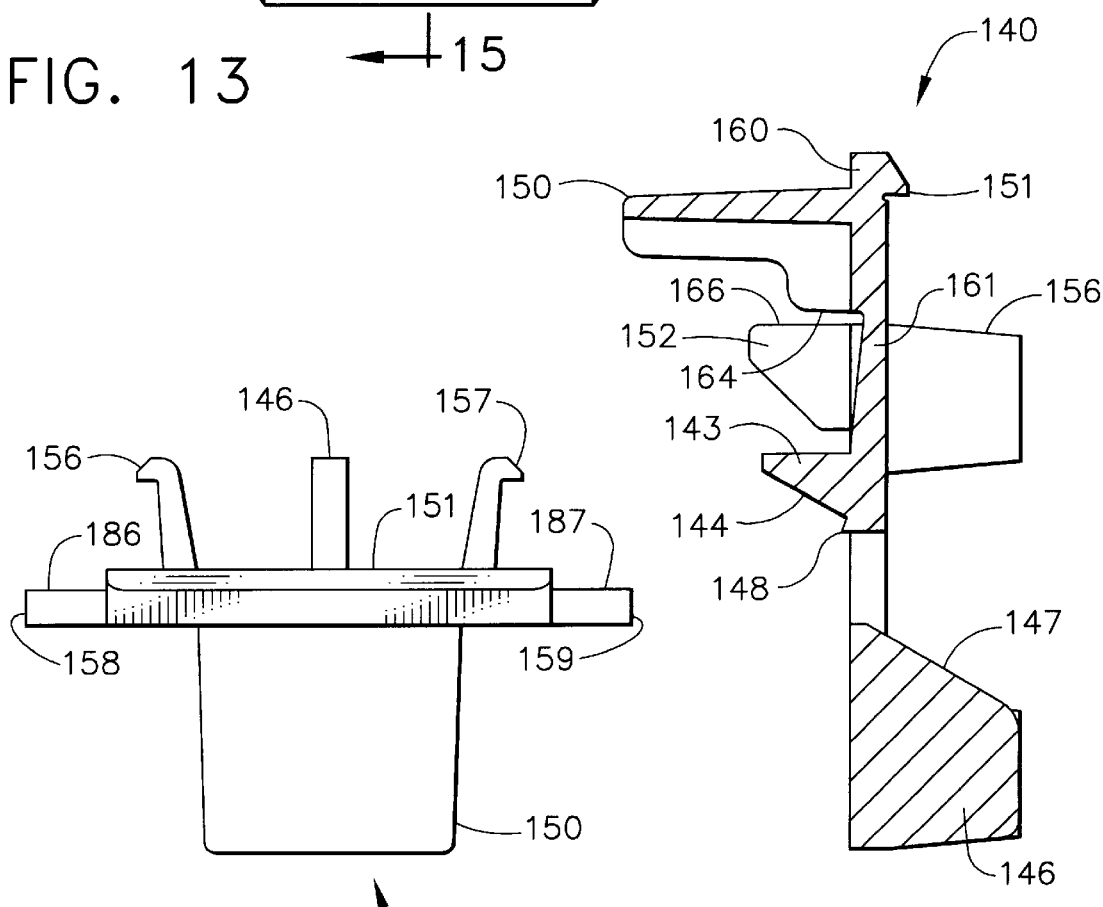
FIG. 14
FIG. 15

DEVICE USED WITH A SURGICAL
RETRACTOR TO ELEVATE BODY PARTS

FIELD OF THE INVENTION

The present invention generally relates to surgery. More specifically, the present invention relates to surgical retractors for temporarily providing access to portions of the internal anatomy such as the thoracic cavity.

BACKGROUND OF THE INVENTION

In traditional methods for performing coronary artery bypass surgery, a segment of a blood vessel is harvested from another portion of the body and is used as an autogenous graft. The graft is typically sutured onto the coronary artery so as to bypass the stenosed area and restore adequate blood flow distal to or downstream from the blockage. Often in such a procedures, the saphenous vein is harvested from the surgical patient's leg and subsequently used as the graft vessel. In a large number of cases, the wound created in the leg is slow to heal and the patient endures considerable pain and irritation. In addition, surgeons have learned that, in general, an artery rather than a vein serves as a better, long term bypass graft.

Many surgeons prefer to use one of the internal mammary arteries (IMA) as the bypass graft. The descending IMA's are located within the thoracic cavity of the patient along each side of the sternum of the rib cage. The IMA is in close proximity to the heart and therefore it is not necessary to completely remove it from the patient. To prepare the IMA, the side branches of the IMA are first hemostatically severed and the main trunk of the vessel is occluded with a clamp. The IMA is then severed at a point just above to the patient's diaphragm so that it is mobilized. However, the IMA is never disconnected from its original blood supply. The freed end of the IMA is then anastomosed to a coronary artery, such as the left anterior descending (LAD) coronary artery, just distal to the stenosis. This procedure requires significant access and visibility into the upper thoracic cavity for the surgeon. The surgeon must free the IMA from the "ceiling" or wall of the internal thoracic cavity, while at the same time being very careful not to puncture or otherwise traumatize the IMA. The side branches of the IMA must be located and transected, usually by using an electrosurgical device, with minimal blood loss.

The most commonly used method of access to the thoracic cavity for the mobilization of the IMA and the anastomosis of it to the LAD coronary artery is a medial sternotomy. For this procedure, a longitudinal incision is made through the patient's sternum on the midline of the chest. Then a surgical retractor is used to spread and hold apart the left and right rib cages, creating an opening which is about four inches wide. The muscles and other tissues of the chest wall are significantly traumatized by this procedure, and the post-operative healing process for the rejoining of the split sternum is sometimes very slow. As a result, the patient endures significant pain and the recovery time is long. In some cases there are significant complications and occasionally follow-up surgical procedures are required.

In recent years, new methods of access into the thoracic cavity have been developed. One minimally invasive method is called a mini-thoracotomy and involves access through an incision running intercostally (between two ribs) of the left chest wall. A surgical retractor, such as the one used for a traditional sternotomy, is used, but in this case the superior and inferior rib cages of the left chest are only spread apart about two inches, thus resulting in much less overall trauma to the bones, muscles, and other tissues in the chest. Subsequently, the patient endures less pain and irritation following the surgery, and the recovery time is significantly decreased.

The mini-thoracotomy method of access to the thoracic cavity, however, has propagated the need for new surgical tools and methods because the opening into the thoracic cavity is considerably smaller than for the sternotomy. Also, since the IMA is attached to the thoracic cavity wall, the angle of approach the surgeon must use through the opening is very difficult since the inferior rib cage tends to obstruct the manipulation of surgical devices used for the procedure. Many of the new surgical retractors used in thoracic surgery have a rib elevator, which tilts the retractor at an angle so as to give the surgeon better access to the thoracic cavity. However, because of this change in the retractor to thoracic surgery, hospitals must now stock both the new retractors and the traditional retractors used in medial sternotomies.

There has, therefore, been a need for a device that can elevate surgical retractors at angles, but which are separate from and readily attachable to such retractors. In addition, there has been a need for such a device which is adaptable for use with many of the commercially available surgical retractors. Furthermore, there is a need for such a device which is easy and quick to set-up, given the importance of minimizing the length of time of the surgical procedure. Also, considering the high cost of surgical procedures today, it is important that such a device be easy to clean and sterilize for reuse, or that it be low cost and disposable.

Finally, there is a surgical need for a device which can be attached to any of numerous surgical retractors in use today, which can provide another means for support or attachment of other surgical devices used in the procedure. Often the surgeon wishes to hold or stabilize an organ or tissues within the cavity, and attach or support an ancillary holding tool on a fixed structure so that an assistant does not have to maintain the position of the holding tool throughout the procedure. Yet the surgical retractor arms are too far away from the organ or tissue of interest to be used as a platform. What is needed is a bar or bridge that can attach to the arms of the surgical retractor and cross over the opening nearer to the organ or tissue of interest. Then this bridge can be used as a platform for supporting or attaching the ancillary holding device.

SUMMARY OF THE INVENTION

In accordance with the present invention, there is provided a device for pivoting a surgical retractor with respect to a patient it is being used on. The device includes a bridge having distal and proximal ends wherein a distal coupling is attached to the distal end of the bridge and a proximal coupling is slidably attached to the bridge proximal to the distal coupling. The proximal and distal couplings include a means for releasably attaching itself to a surgical retractor. The device further includes a lifting assembly attached to the bridge proximal to the proximal coupling. The lifting assembly comprises a means for applying an upward force to the proximal coupling, whereby when the device is attached to a surgical retractor, the lifting assembly pivots the retractor upward about the distal coupling.

BRIEF DESCRIPTION OF DRAWINGS

While the specification concludes with claims which particularly point out and distinctly claim the subject matter forming the present invention, it is believed that the invention will be better understood from the following description of the preferred embodiment taken in conjunction with the accompanying drawings wherein:

FIG. 3 is a front elevational view of the rib lifting apparatus 20 depicted in FIG. 2;

FIG. 4 is a top elevational view of the rib lifting apparatus 20 depicted in FIG. 2;

FIG. 8 is a front elevational view of the bridge assembly 168 of the alternate embodiment of the present invention depicted in FIG. 7;

FIG. 9 is a bottom elevational view of the bridge assembly 168 of the alternate embodiment of the present invention depicted in FIG. 7;

FIG. 11 is longitudinal sectional view 11—11 of the tower depicted in FIG. 10;

FIG. 12 is transverse sectional view 12—12 of the tower depicted in FIG. 10;

FIG. 13 is a front elevational view of the elevator of the alternate embodiment of the present invention depicted in FIG. 7;

FIG. 14 is a top elevational view of the elevator of the alternate embodiment of the present invention depicted in FIG. 7; and FIG. 15 is longitudinal sectional view 15—15 of the elevator depicted in FIG. 13.

The drawings are not necessarily to scale.

DETAILED DESCRIPTION OF THE INVENTION

Figure 1:
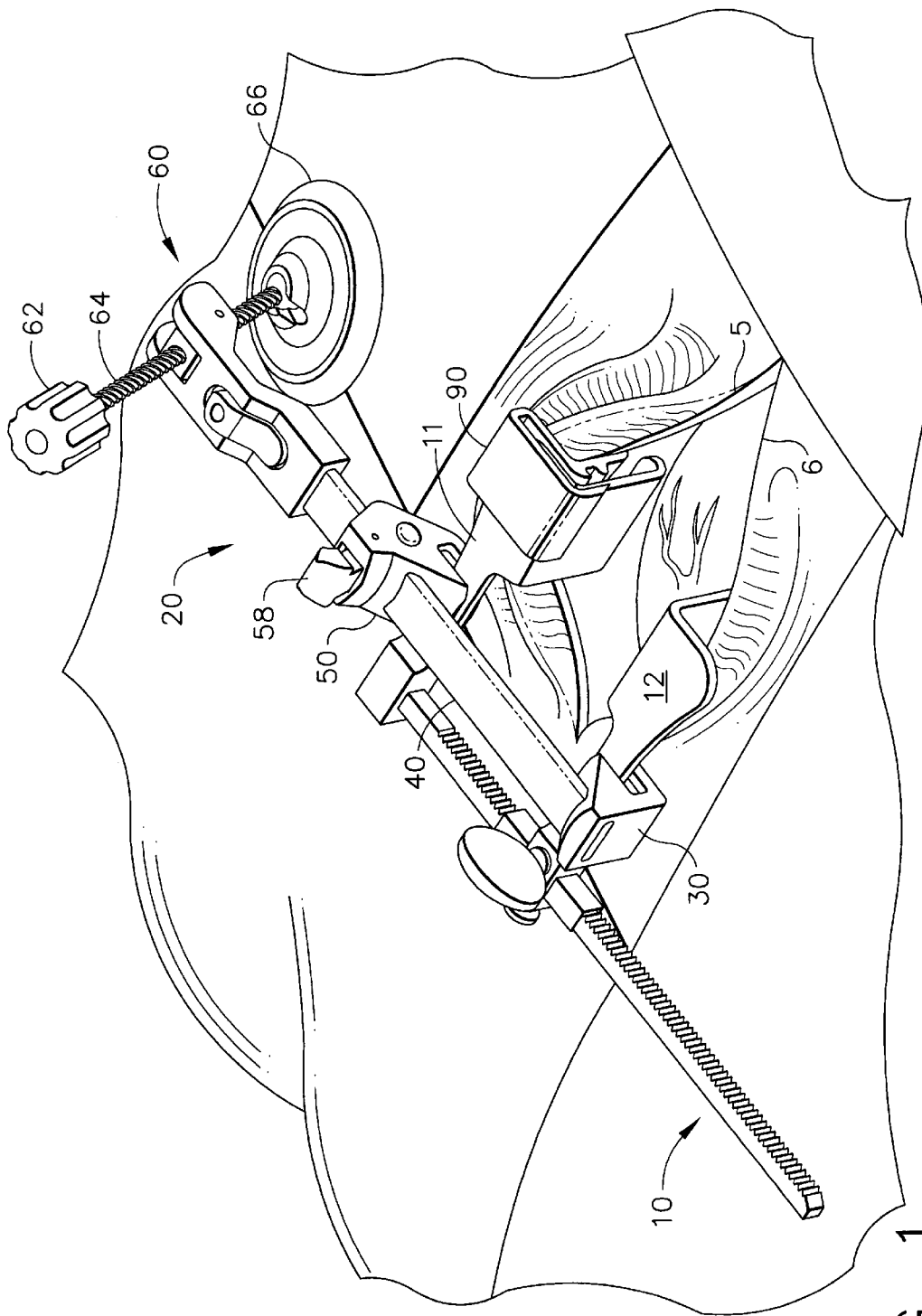
FIG. 1 is a perspective view of the present invention as it is used in conjunction with a surgical retractor on a chest wall incision on a surgical patient.

The present invention described herein can be used in conjunction with a number of commercially available, reusable, surgical retractors for improving access into the thoracic cavity. There is shown in FIG. 1, a rib lifting device 20 which serves as a lever for tilting retractor 10 at an angle. Device 20 comprises a distal coupling, which in this embodiment is shown as hook 30, a bridge 40, a slideable proximal coupling, which in this embodiment is shown as hook 50, and a lifting sub-assembly 60. The distal hook 30 is attached to the distal arm 12 of the surgical retractor 10 and serves as the fulcrum for the lever system. Bridge 40 is attached to the proximal arm 11 of the surgical retractor 10, thereby retracting the superior and inferior rib cages 5 and 6, respectively. An upward force is applied to the proximal hook 50 by the lifting subassembly 60 so that the entire system pivots upward about the distal hook 30, and thereby lifts the superior rib cage 5 above the inferior rib cage 6. It should be appreciated that the present invention could be used in the reverse manner, if the surgeon preferred, in which the inferior rib cage 6 is lifted above the superior rib cage 5. It should also be appreciated that the present invention can be used for a medial sternotomy as well as the thoracotomy. In FIG. 1, the arm extender 90 is slideably attached to the proximal arm 11 of the surgical retractor 10, so that the blade 92 (see FIG. 5) is reliably supporting the superior rib cage 5 from underneath.

Still referring to FIG. 1, it can be seen that the surgical retractor shown, as for all commercially available surgical retractors of this type, has a means for mechanically adjusting the distance between the proximal and distal arms 12 and 11, respectively. Therefore it is necessary for the rib lifting device 20, which is attached to surgical retractor 10, to have also a means of adjustment of the distance between the distal and proximal hooks 30 and 50, respectively. Also it can be seen that a means for adjusting the elevation of the superior rib cage 5 over the inferior rib cage 6 has been provided so that the surgeon can adjust the size of the opening into the thoracic cavity with minimal trauma to the surgical patient. Knob 62 is turned by the surgeon or an assistant to advance the screw 64 while the foot 66 bears against the chest of the surgical patient. The foot 66 is distanced somewhat superior to blade 92 (see FIG. 5) of the arm extender 90 so that an effective lifting force can be applied to the proximal hook 50 by the lifting subassembly 60.

The present invention may also be assembled to the surgical retractor 10 in the reverse manner to that shown in FIG. 1, without change to its usage or function. The physical anatomy of the surgical patient and the requirements of the surgical procedure would dictate in which direction to assemble it.

Figure 2:
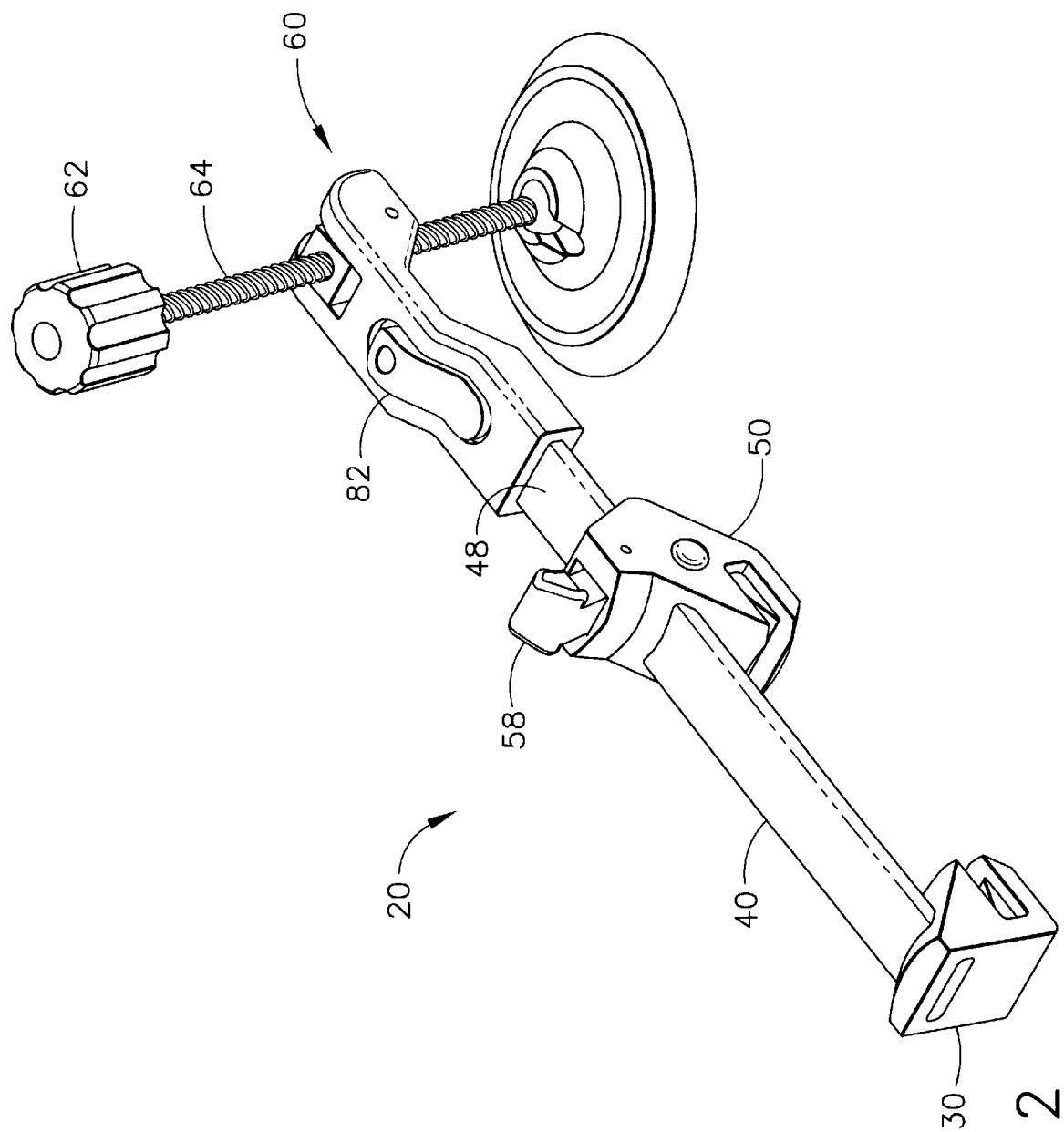
FIG. 2 is a perspective view of the rib lifting apparatus 20 of the present invention depicted in FIG. 1.

Turning now to FIG. 2, the rib lifting device 20 is shown without the extender 90 and the surgical retractor 10 for clarity. The rib lifting device has three actuators for its attachment and detachment to the surgical retractor: a slide lock lever 58 for locking the proximal hook 50 onto the bridge 40 or for unlocking it from the bridge in order to adjust the distance between the distal and proximal hooks, 30 and 50, respectively; a release button 82 for detaching the lifting subassembly 60 from the proximal end 48 of the bridge 40; and a screw knob 62 for rotating screw 64 for lifting or lowering the proximal hook 50.

FIGS. 3 and 4 are front and top views, respectively, of the rib lifting device depicted in FIG. 2. Distal hook 30 may be attached to the distal end 46 of the bridge 40 by a press fit, by use of fasteners, or by a number of other means well-known to those skilled in the art. Integrally situated in distal hook 30 and spaced at a optimal distance vertically beneath the bridge 40 is V-groove 32 for the insertion of surgical retractor arm 12. Slideably mounted on the bridge 40 is proximal hook 50 which also has a V-groove 52 directly opposing the V-groove 32 on the distal hook 30. The lever 58 is raised to an up-position to allow the movement of the proximal hook 50 along the bridge 40. Indentations 54 (front and back side of proximal hook) aid the surgeon in gripping the proximal hook to position it on the surgical retractor. When the retractor arms 11 and 12 (see FIG. 1) of the surgical retractor are captured within the opposing V-grooves 32 and 52, the lever 58 is pushed down to lock the position of the proximal hook onto the bridge 40. Lever 58 pivots about lever pivot 56 and cams against the posterior surface 42 ol the bridge 40, thus locking the proximal hook to the bridge.

Still referring to FIGS. 3 and 4, proximal end 48 of bridge 40 is inserted into lifting frame 80. An indentation (not visible) on bottom surface 44 on the proximal end 48 of the bridge latches with a projection (not visible) off of button 82 which is spring biased in the latching position. This attachment may be released by pressing button 82 and withdrawing the bridge 40 from the frame 80. The ability of the rib lifting device to disassemble in this way is advantageous for the shipping, handling, and cleaning of the device, and also for the use of the bridge and hooks separately as will be described later for the alternate embodiment of the present invention. Integral with lifting frame 80 is lifting frame fork 84 which holds swivel block 70. The swivel block pivots about swivel pins 72, 73 (pin 72 visible only) and contains an internal screw thread for receiving screw 64. As described earlier, knob 62 is attached to screw 64. On the opposite end of the screw 64 is affixed ball 68 which in turn is captured within a cup 69 integral with foot 66. The screw is constrained by the swivel block 70 to an optimal angular variation within the plane defined by the longitudinal axis through it and the bridge 40. The range of motion for the screw 64 with respect to the foot 66 is generally conical due to the ball and cup attachment described. All of the components for the rib lifting device 20 described for FIGS. 3 and 4 may be made from various metals such as stainless steel, or from various, rigid, medical grade plastics, or from a combination of metal and plastics. The device can be manufactured to be reusable or single-patient-use disposable.

Figure 5:
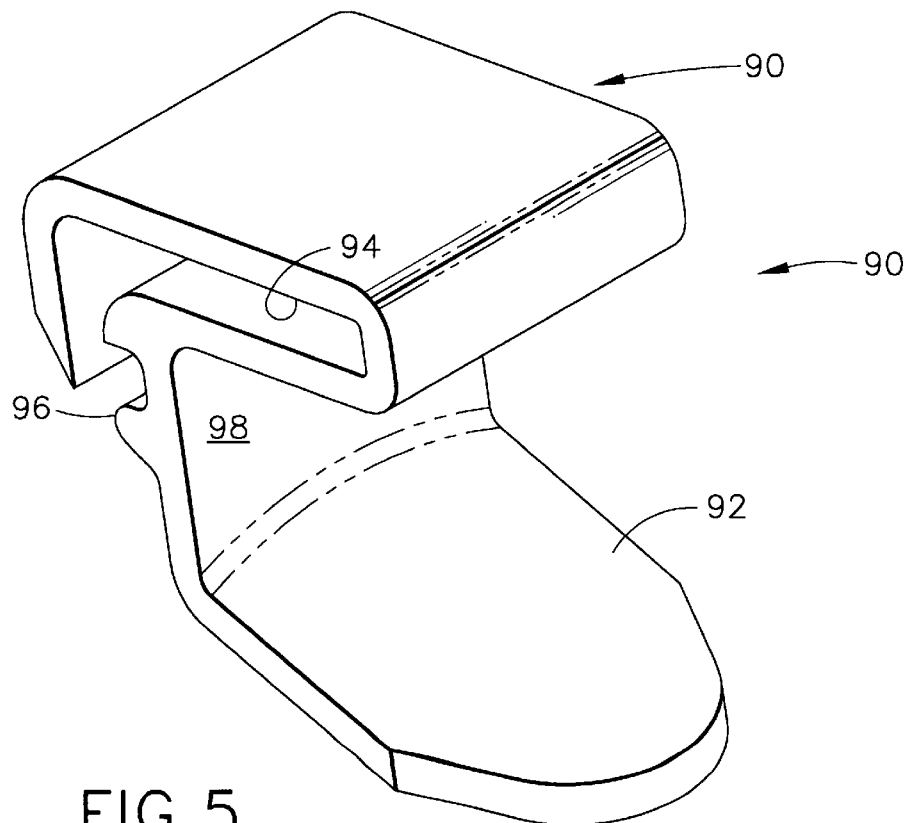
FIG. 5 is a perspective view of the arm extender 90 of the present invention depicted in FIG. 1.
Figure 6:
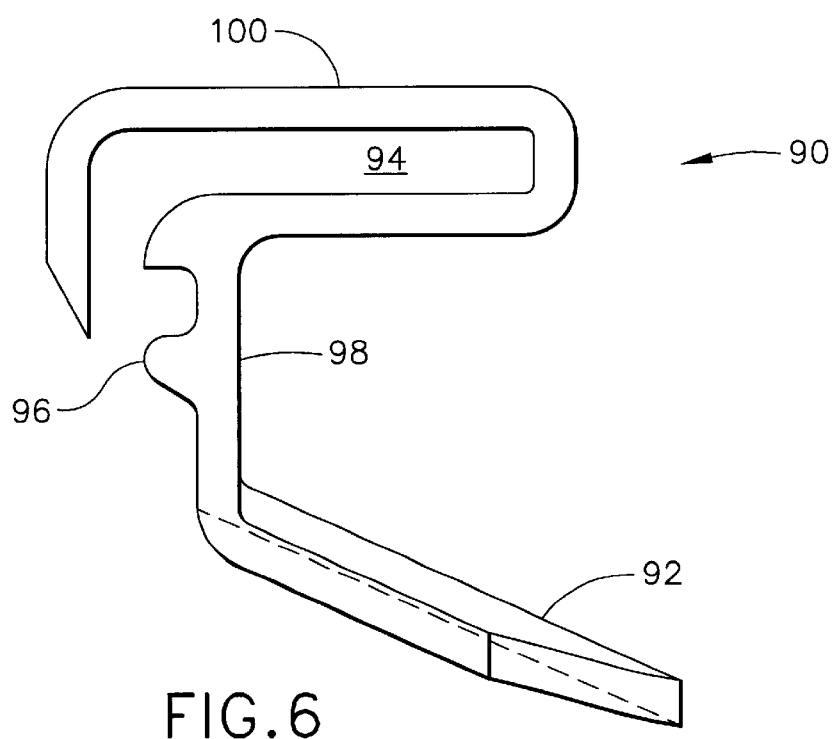
FIG. 6 is a front elevational view of the arm extender 90 of the present invention depicted in FIG. 1.

Now referring to FIGS. 5 and 6, the arm extender 90 is seen to consist of one piece which may be made of metal, preferably stainless steel, or of a rigid, medical grade plastic. Arm extender 90 is comprised of a blade 92, a vertical span 98, an arm wrap 100 forming an L-shape slot 94, and a fin 96. Blade 92 is designed to extend underneath the rib cage (see FIG. 1) so that an upward force can be applied by the rib lifting device without the arm extender slipping off the edge of the surgical incision in the chest wall. It also distributes the lifting force over a broad area of tissue and/or bones so as to minimize trauma to the delicate tissue lining the internal, thoracic cavity. Variation of the length of vertical span 98, the length of blade 92, and the angle between, is advantageous to the surgeon for accommodating variations in the surgical patients. Therefore a set of these arm extenders, each having a different geometry in these aspects, may be provided from which the surgeon may choose. The L-slot 94 is sized to fit slideably over many different sizes and kinds of commercially available, surgical retractors. The L-slot, together with the fin 96, prevent the arm extender from rotating about the arm of the surgical retractor, so as to transmit the upward force to the chest wall.

Figure 7:
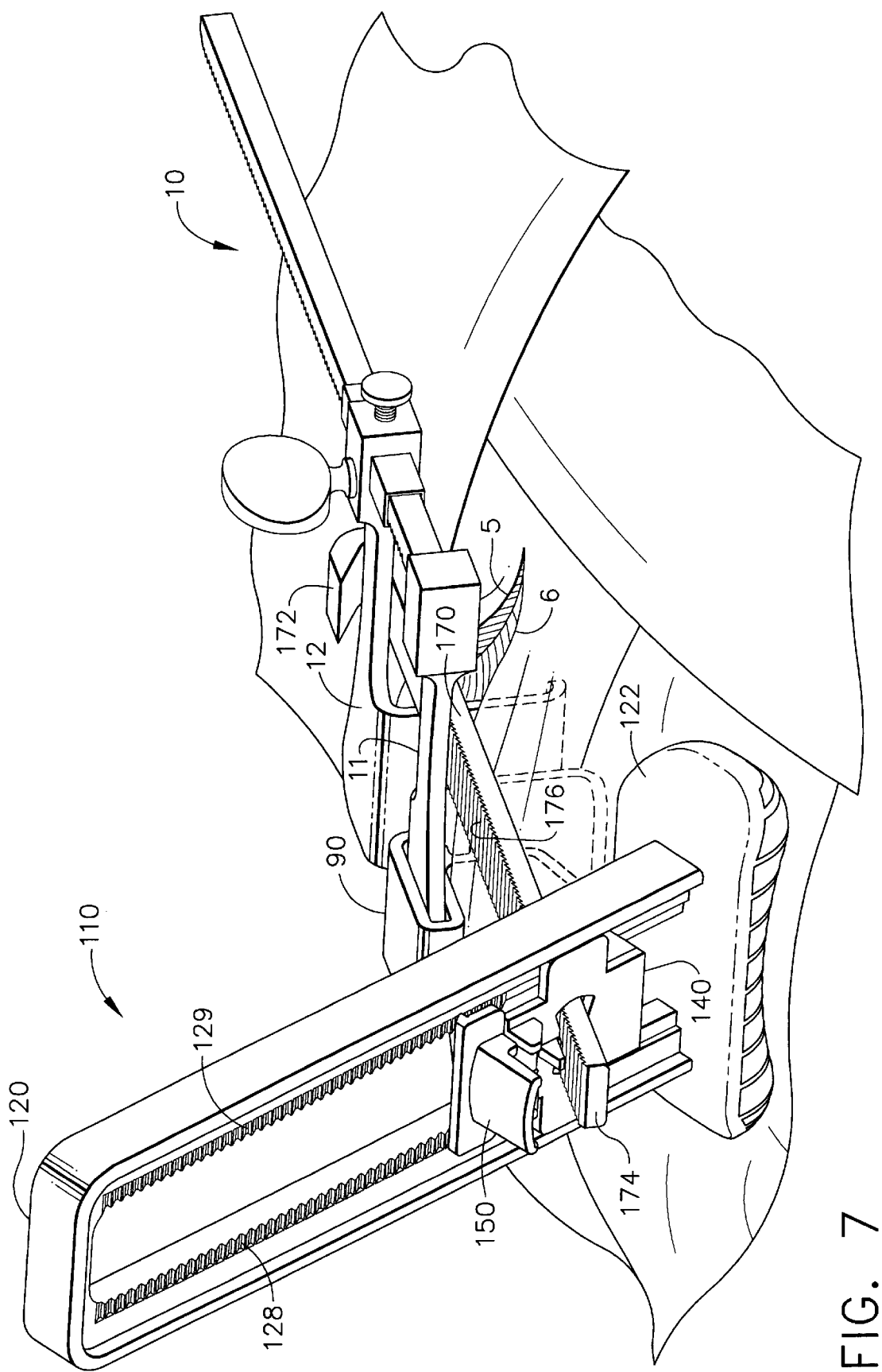
FIG. 7 is a perspective view of an alternate embodiment of the present invention, being used in conjunction with a surgical retractor on a surgical patient.

Referring now to FIG. 7, an alternate embodiment of the present invention is shown being used in conjunction with a surgical retractor on a surgical patient. This embodiment is much like the other in that it tilts the plane of the anatomical opening into the body cavity so that access and visibility within is enhanced. The primary difference of the alternate embodiment is that the same function is accomplished as before, but with fewer components. As will become apparent, the alternate embodiment also has a different method of assembly during the surgical procedure. The alternate embodiment of the present invention is the rib lifting device 110 depicted in FIG. 7, comprising a bridge 170, a tower 120, an elevator 140, and an arm extender 90. Distal hook 172 of bridge 170 hooks and passes beneath retractor arm 12 of surgical retractor 10. This junction serves as the fulcrum of the lever system of the present invention. Bridge 170 passes also beneath arm 11 of the surgical retractor 10 and thus is positioned to lift the arm 11 and the superior rib cage 6 attached thereto above the inferior rib cage 5. The proximal end 174 of bridge 170 is supported within elevator 140 which in turn is adjustably mounted within tower 120. Preferably, bridge 170 can axially rotate about its longitudinal axis, extending between the distal and proximal ends, with respect to or independent of the lifting assembly. Base 122 of tower 120 bears against the chest of the surgical patient. The elevator 140 contains a locking feature to be described later which engages with ratchet teeth 176 of bridge 170 only when the tower 120 is tilted superior with respect to the bridge 170 at an angle of approximately thirty degrees past vertical, as is shown in FIG. 7. When the tower 120 is vertical and its longitudinal axis is essentially perpendicular to the longitudinal axis of the bridge 170, then it is possible to move the tower along the length of the bridge so as to position the base 122 of the tower on the chest of the surgical patient, or to remove the tower from the bridge 170. This adjustment is easily accomplished while the elevator 140 is in the lowered position within tower 120, because the force of the bridge 170 against the retractor arm 11 is minimal. Once the base 122 of the tower 120 is properly located on the chest of the surgical patient, the elevator may be manually raised by the surgeon or surgical assistant by lifting up on the proximal end 174 of the bridge 170. A locking mechanism, to be described later, of the elevator 140 engages with the ratchet teeth 128, 129 of the tower 120 in order to maintain the vertical position of the elevator 140 during the surgical procedure. To release this lock, the release button 150 may be pushed downwardly and the elevator falls immediately to a lower position within the tower 120 due to the downward force exerted by the arm 11 of the retractor 10. At this point the tower 120 can be repositioned, and then the elevator 140 raised again, or the device may be disassembled from the surgical retractor 10.

The arm extender 90 depicted in FIG. 7 is identical in form and function to that which is depicted in FIG. 1.

FIGS. 8 and 9 show the bridge 170 depicted in FIG. 7 assembled with slide 180 (not shown in FIG. 7), hereinafter referred to as the bridge assembly 168. Specifically, the bridge assembly 168 becomes an advantageously located platform for attaching other surgical devices or simply as a support for the hand of the surgeon or surgical assistant. Here the hooks 172 and 182 of the bridge assembly 168 are facing downward towards the surgical patient and capturing the arms 12 and 11 respectively of the surgical retractor 10. Referring to FIG. 8, the bridge 170 is inserted through a rectangular, longitudinal hole in the slider frame 183. This hole is large enough to allow some angular movement of the bridge 170 within the slider 180 in the vertical, longitudinal plane. When the slider is pushed against the retractor arm 11 so that the arm presses firmly against hook 182, the slide lock pawl 184 engages the bridge ratchet teeth 176 to lock the slider in place. The same result occurs when the slider is held in place while the retractor arms 11 and 12 are spread apart slightly. The lock can easily be released by either adjusting the retractor arms to a smaller width than before, or by pressing down on the top of the slider 180 to rock the pawl 184 from engagement with the ratchet teeth 176. The bridge 170 and the slider 180 may be made of a metal such as stainless steel, or from a medical grade, rigid plastic such as a glass-filled polyetherimide. The slider 180 is not intended for use on the bridge 170 while the tower 120 is attached.

Figure 10:
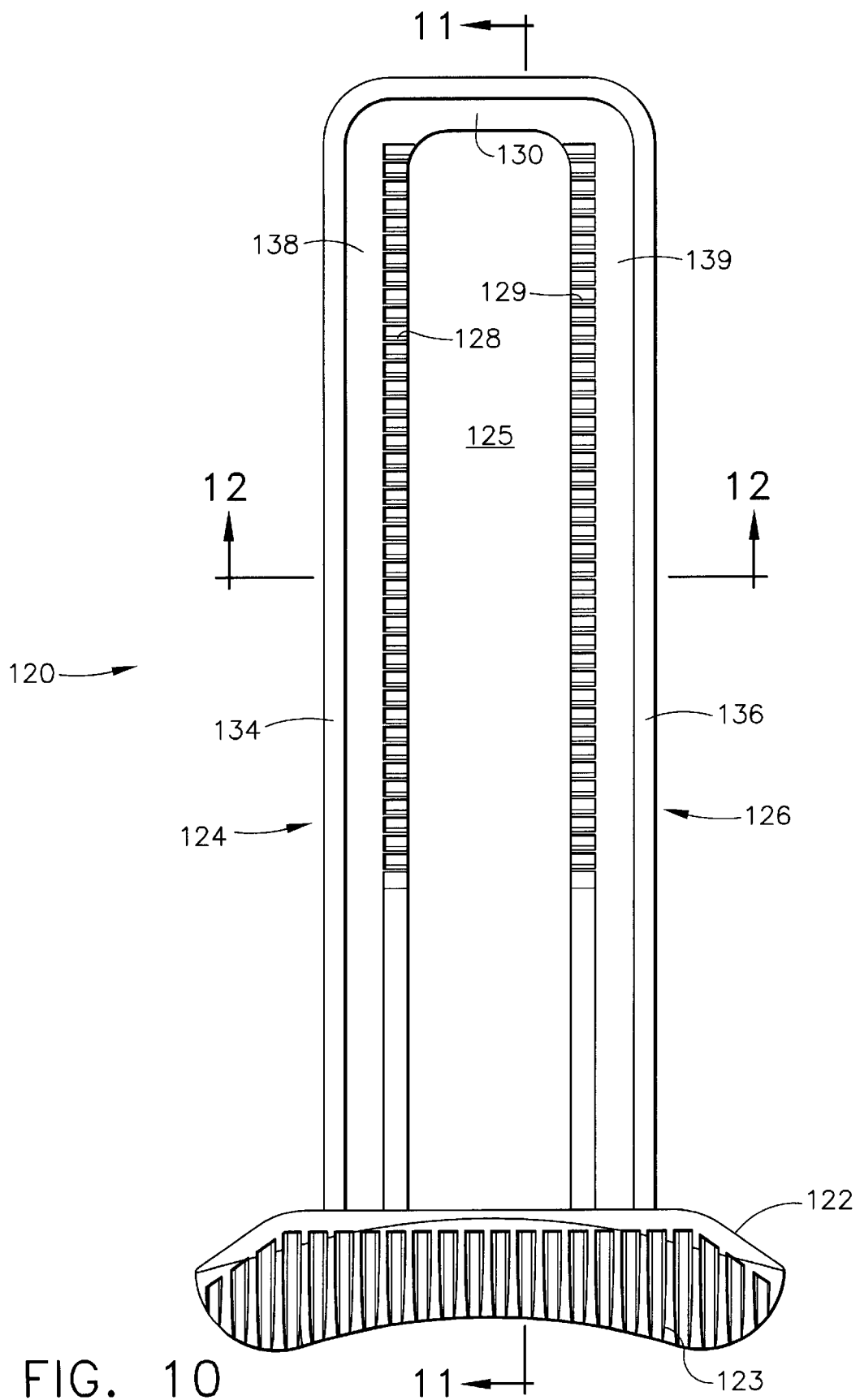
FIG. 10 is a front elevational view of the tower of the alternate embodiment of the present invention depicted in FIG. 7.

Next is described the features of the tower 120 and elevator 140 which work in concert to supply a upward holding force to the proximal end 174 of the bridge 170. These features can best be viewed in FIGS. 10 through 15. In FIG. 10 is a front view of the tower 120 which comprises a left column 124, a right column 126, joined at the top by cornice 130, and at the bottom by base 122. The columns 124 and 125 form an essentially rectangular opening 125. On the front of left column 124 is vertical left rail 134 which runs around cornice 130 to join vertical right rail 136 on right column 126. Also on left column 124 is a vertical array of ratchet teeth 128, and likewise on the right column are ratchet teeth 129. As can be seen in longitudinal cross section view 11—11 of FIG. 11, these teeth are designed to allow a pawl to slide freely when moving in the upward direction, but to lock in the downward direction. In FIGS. 10 and 11 the base 122 is shown to consist of a plurality of fins 123 which facilitate the injection molding of the tower 120 from a rigid, medical grade plastic such as glass-filled polyetherimide. It may also be made of a metal such as stainless steel.

FIG. 12 is lateral cross-sectional view 12—12 depicted in FIG. 10. In this view are shown left and right second rails, 135 and 137, respectively, which serve to capture the elevator 140. Rails 134 and 136 are again shown to indicate the front of the tower 120 as the top of this cross-sectional view.

The elevator 140 is shown in FIGS. 13, 14, and 15 and comprises a frame 141 (FIG. 13), extending from which is a T-beam 160, left wing 162, right wing 163, left lever stop 152, right lever stop 153, upper projection 143, lower projection 146, left lower latch 154, left upper latch 156, right lower latch 155, and right upper latch 157. Centered on frame 141 is bow-tie slot 142. Extending from the front of T-beam 160 is release lever 150, and extending from the back of T-beam 160 is pawl rib 151.

The elevator 140 is slideably attached to tower 120 by the four latches, 154–157, which are flexible cantilevers. These latches are aligned and then inserted into the front of opening 125 of the tower 120. The latches snap around the edges of rails 135 and 137 of the tower (FIG. 12) so that guide edges 158 and 159 on the elevator 140 are closely interposed between rails 134 and 136 of the tower. Left and right wing surfaces 186, 187, slide against left and right sliding surfaces 138, 139, respectively, of the tower 120.

Once assembled to tower 120, pawl rib 151 can engage with left and right ratchet teeth 128, 129 of the tower to maintain the vertical position of the elevator 140. The elevator can be raised in the tower most easily by pulling up on the bridge 170 which is inserted through bow-tie slot 142. T-beam portion 161 flexes as the pawl rib 151 rides over the ratchet teeth 128, 129. To release the pawl rib from the ratchet teeth, the surgeon or surgical assistant may press down on the release button 150 and the elevator will immediately fall to its lowest position in the tower. Left and right stop surfaces 166, 167 of the left and right lever stops 152, 153, respectively, serve to prevent over-flexure of the T-beam portion 161 when the release button 150 is depressed.

The proximal end 174 of bridge 170 (see FIG. 8) fits loosely through bow-tie slot 142 when the longitudinal axis of the bridge 170 is normal to the plane of the elevator frame 141. The ratchet teeth 176 are to face upward when the bridge 170 is assembled with the elevator 140. (As previously noted, slide 180 of FIG. 8 is not to be used with the elevator and tower.) Due to the bow-tie slot shape, the bridge is permitted to rotate slightly in both directions about its longitudinal axis. This allows the surgeon a wide range of variation in the assembly of the present invention to the surgical retractor 10, and is necessary due to the curvature of the chest of the surgical patient. As described earlier, when the tower and the elevator contained within it are tilted about 30 degrees past the perpendicular formed with the longitudinal axis of the bridge 170, the elevator becomes locked on the teeth 176 of the bridge. Bridge pawl 148 is seen in FIGS. 13 and 15 and only engages the bridge teeth 176 at the angle described. Stop surface 144 of the upper projection 143 and stop surface 147 of the lower projection 146 serve to limit the maximum amount of tilt of the elevator 140 and tower 120. The elevator 140 may be made from a metal such as stainless steel, but the preferred material is a medical grade, rigid plastic such as polyetherimide.

The method described for locking the bridge to the tower by tilting the tower thirty degrees from its perpendicular position to the bridge to allow the bridge pawl 148 to engage the bridge teeth 176 on the bridge is only one of various methods for doing so, as can be appreciated by those skilled in the art. For example, another method would be to fashion a spring biased release mechanism on the elevator 140 which automatically engages the bridge teeth 146 when the tower is assembled to the bridge. The angle the tower makes with the bridge would not matter, and in fact, an optimal, fixed angle of assembly could be incorporated. A pawl on this release mechanism on the elevator could ratchet over the bridge teeth as the tower is moved towards the distal end of the bridge, but could only move proximally upon actuation of the release mechanism.

The alternate embodiment of the present invention can also be made to be reusable or single-patient-use disposable.

From the foregoing, it will be observed that numerous modifications and variations can be effected without departing from the true spirit and scope of the novel concept of the present invention. It is to be understood that no limitation with respect to the specific embodiments illustrated herein is intended or should be inferred. The disclosure is intended to cover by the appended claims all such modifications as fall within the scope of the claims.

What is claimed is:

1. A device for pivoting a surgical retractor with respect to a patient it is being used on, said device comprising:
    a) a bridge having distal and proximal ends, a distal coupling attached to said distal end of said bridge and a proximal coupling slidably attached to said bridge proximal to said distal coupling, each of said proximal and distal couplings comprising means for releasably attaching itself to a surgical retractor; and
    b) a lifting assembly attached to said bridge proximal to said proximal coupling, said lifting assembly comprising a means for applying an upward force to said proximal coupling whereby when said device is attached to said surgical retractor, said lifting assembly can pivot said retractor upward about said distal coupling.

2. The device according to claim 1 wherein said distal and proximal couplings comprise hooks for receiving arms of said retractor.

3. The device according to claim 1 wherein said proximal coupling further includes a releasable lock to secure said proximal coupling to said retractor.

4. The device according to claim 1 wherein said lifting assembly is detachable from said bridge.

5. The device according to claim 4 wherein said proximal coupling is attached to said lifting assembly.

6. The device according to claim 1 wherein said lifting assembly comprises:
    a) a foot for pressing against a substantially stationary object;
    b) a threaded screw extending upwardly from said foot;
    c) a lifting frame extending radially from said screw, said frame having threads receiving said screw in threaded engagement, said frame further including a means for attaching said frame to said bridge.

7. The device according to claim 6 wherein said screw is attached to said foot by a ball and socket connector.

8. The device according to claim 6 further including a knob on an upmost portion of said screw for adjusting the position of said frame with respect to said screw.

9. The device according to claim 6 further including a means for pivoting said frame with respect to said screw.

10. The device according to claim 1, wherein said lifting assembly can change its proximal position relative to said distal coupling.

11. An apparatus for providing access to portions of the human anatomy, said apparatus comprising:
    a) a retractor, having proximal and distal arms, and a means for adjusting the distance between said proximal and distal arms; and
    b) a device for pivoting a surgical retractor with respect to a patient it is being used on, said device comprising:
        i) a bridge having distal and proximal ends, a distal coupling attached to said distal end of said bridge and a proximal coupling slidably attached to said bridge proximal to said distal coupling, each of said proximal and distal couplings comprising means for releasably attaching itself to said proximal and distal arms of said retractor; and ii) a lifting assembly attached to said bridge proximal to said proximal coupling, said lifting assembly comprising a means for applying an upward force to said proximal coupling whereby when said device is attached to said surgical retractor, the lifting assembly pivots said retractor upward about the distal coupling.

12. The apparatus according to claim 11 further including an arm extender, said arm extender comprising a means for releasably attaching itself to one of said arms of said retractor, and a blade which extends outwardly from said arm when attached thereto.

13. The apparatus according to claim 12, wherein said arm extender is slidably attached to said arm.

14. The device according to claim 11 wherein said distal and proximal couplings comprise hooks for receiving arms of said retractor.

15. The device according to claim 11 wherein said proximal coupling further includes a releasable lock to secure said proximal coupling to said retractor.

16. The device according to claim 11 wherein said lifting assembly is detachable from said bridge.

17. The device according to claim 16 wherein said proximal coupling is attached to said lifting assembly.

18. The device according to claim 11 wherein said lifting assembly comprises:
   a) a foot for pressing against a substantially stationary object;
   b) a threaded screw extending upwardly from said foot;
   c) a lifting frame extending radially from said screw, said frame having threads receiving said screw in threaded engagement, said frame further including a means for attaching said frame to said bridge.

19. The device according to claim 18 wherein said screw is attached to said foot by a ball and socket connector.

20. The device according to claim 18 further including a knob on an upmost portion of said screw for adjusting the position of said frame with respect to said screw.

21. The device according to claim 18 further including a means for pivoting said frame with respect to said screw.

22. The device according to claim 11, wherein said lifting assembly can change its proximal position relative to said distal coupling.

23. A device for pivoting a surgical retractor with respect to a patient it is being used on, said device comprising:
   a) a bridge having distal and proximal ends, a distal coupling attached to said distal end of said bridge and a proximal coupling slidably attached to said bridge proximal to said distal coupling, each of said proximal and distal couplings have a mechanism for releasably attaching itself to a surgical retractor; and
   b) a lifting assembly attached to said bridge proximal to said proximal coupling, said lifting assembly comprising a mechanism for applying an upward force to said proximal coupling whereby when said device is attached to said surgical retractor, said lifting assembly can pivot said retractor upward about said distal coupling.

24. The device according to claim 23 wherein said distal and proximal couplings comprise hooks for receiving arms of said retractor.

25. The device according to claim 23 wherein said proximal coupling further includes a releasable lock to secure said proximal coupling to said retractor.

26. The device according to claim 23 wherein said lifting assembly is detachable from said bridge.

27. The device according to claim 26 wherein said proximal coupling is attached to said lifting assembly.

28. The device according to claim 23 wherein said lifting assembly comprises:
   a) a foot for pressing against a substantially stationary object;
   b) a threaded screw extending upwardly from said foot;
   c) a lifting frame extending radially from said screw, said frame having threads receiving said screw in threaded engagement, said frame further including a means for attaching said frame to said bridge.

29. The device according to claim 28 wherein said screw is attached to said foot by a ball and socket connector.

30. The device according to claim 28 further including a knob on an upmost portion of said screw for adjusting the position of said frame with respect to said screw.

31. The device according to claim 28 further including a means for pivoting said frame with respect to said screw.

32. The device according to claim 23 wherein said lifting assembly can change its proximal position relative to said distal coupling.

33. An apparatus for providing access to portions of the human anatomy, said apparatus comprising:
   a) a retractor, having proximal and distal arms, and a means for adjusting the distance between said proximal and distal arms; and
   b) a device for pivoting a surgical retractor with respect to a patient it is being used on, said device comprising:
      i) a bridge having distal and proximal ends, a distal coupling attached to said distal end of said bridge and a proximal coupling slidably attached to said bridge proximal to said distal coupling, each of said proximal and distal couplings comprising a mechanism for releasably attaching itself to said proximal and distal arms of said retractor; and
      ii) a lifting assembly attached to said bridge proximal to said proximal coupling, said lifting assembly comprising a mechanism for applying an upward force to said proximal coupling whereby when said device is attached to said surgical retractor, the lifting assembly pivots said retractor upward about the distal coupling.

34. The apparatus according to claim 33 further including an arm extender, said arm extender comprising a means for releasably attaching itself to one of said arms of said retractor, and a blade which extends outwardly from said arm when attached thereto.

35. The apparatus according to claim 34, wherein said arm extender is slidably attached to said arm.

* * * * *